(12) United States Patent
Serikawa et al.

(10) Patent No.: US 8,781,758 B2
(45) Date of Patent: Jul. 15, 2014

(54) OPTICAL INSPECTION METHOD AND ITS APPARATUS

(75) Inventors: Shigeru Serikawa, Kamisato (JP); Bin Abdulrashid Fariz, Kamisato (JP); Keiji Kato, Kamisato (JP)

(73) Assignee: Hitachi High-Technologies Corporation, Tokyo (JP)

( * ) Notice: Subject to any disclaimer, the term of this patent is extended or adjusted under 35 U.S.C. 154(b) by 332 days.

(21) Appl. No.: 13/209,555

(22) Filed: Aug. 15, 2011

(65) Prior Publication Data

US 2012/0046885 A1 Feb. 23, 2012

(30) Foreign Application Priority Data

Aug. 20, 2010 (JP) .................. 2010-184863

(51) Int. Cl.
*G01N 21/88* (2006.01)
*G06F 19/00* (2011.01)
*G01N 21/95* (2006.01)
*G01N 21/89* (2006.01)
*G11B 19/04* (2006.01)

(52) U.S. Cl.
CPC .............. *G01N 21/95* (2013.01); *G01N 21/89* (2013.01); *G11B 19/048* (2013.01)
USPC .......... 702/40; 356/237.2; 369/53.17; 702/35

(58) Field of Classification Search
CPC ... G01N 21/95; G01N 21/89; G01N 21/4738; G01N 21/956; G01N 21/9501; G11B 19/048
USPC .......... 702/35, 40, 159, 81; 356/237.2, 237.4, 356/364, 237.3; 369/53.17
See application file for complete search history.

(56) References Cited

U.S. PATENT DOCUMENTS

2002/0080345 A1* 6/2002 Ishiguro ..................... 356/237.2
2008/0239904 A1* 10/2008 Yoshida et al. ............. 369/53.17

FOREIGN PATENT DOCUMENTS

JP  2002-257742 A  9/2002
JP  2008-268189 A  11/2008

* cited by examiner

*Primary Examiner* — John H Le
(74) *Attorney, Agent, or Firm* — Mattingly & Malur, PC

(57) ABSTRACT

The present invention provides an optical inspection method capable of detecting a finer defect in the surface of a substrate, including the steps of: irradiating a surface of a sample which is rotating and continuously moving in one direction with illumination light which is incident in a direction obliquely to the sample surface; detecting an image of light formed by a forward scattering light around an optical axis of regular-reflection light while excluding the regular-reflection light from the sample surface irradiated with the illumination light; condensing and detecting lateral scattering light which scatters laterally from the sample surface with respect to an incidence direction of the illumination light; and processing a signal obtained by detecting the image of light formed by the forward scattering light and a signal obtained by condensing and detecting the lateral scattering light to extract a defect including a scratch defect.

14 Claims, 11 Drawing Sheets

FIG. 7

| DETECTION SYSTEM \ KIND OF DEFECT | FOREIGN MATTER | FOREIGN MATTER | SHALLOW DEFECT |
|---|---|---|---|
| LATERAL SCATTERING LIGHT | ○ | ○ | × |
| REGULAR-REFLECTION LIGHT | ○ | × | ○ |

○ : PRESENCE OF DETECTION SIGNAL
× : ABSENCE OF DETECTION SIGNAL

OPTICAL INSPECTION METHOD AND ITS APPARATUS

BACKGROUND

The present invention relates to a method and apparatus for optically detecting a defect in a sample surface and, more particularly, to an optical inspection method and apparatus suitable for detecting a recess or a flaw in the surface of a conventional magnetic disk and foreign matters adhered to both faces of a magnetic disk.

For example, Japanese Patent Application Laid-Open Publication No. 2002-257742 (hereinbelow, referred to as patent document 1) and Japanese Patent Application Laid-Open Publication No. 2008-268189 (hereinbelow, referred to as patent document 2) describe an apparatus for detecting a defect in a surface of a magnetic disk as a conventional continuous recording magnetic medium. The patent document 1 discloses a configuration of obliquely irradiating a rotating magnetic disk with a laser beam, forming an image by regular-reflection light from the surface of the disk on a detector having plural light receiving elements, and processing a detection signal of the light to detect a defect.

The patent document 2 discloses an inspection apparatus which obliquely irradiates a rotating magnetic disk with a laser beam, detects regular-reflection light and scatting light from the surface of the disk, and processes detection signals of the regular-reflection light and scattering light to detect and classify a defect in the surface of the disk.

The patent document 2 also describes that a mask is provided so that regular-reflection light does not enter a lens provided on the side of regular reflection from a substrate (disk) to thereby interrupt regular-reflection light other than scatting light. It also describes that a half mirror is provided in place of a mask, and regular-reflection light is reflected by the half mirror and detected by a detector.

As the recording capacity of a magnetic disk increases, the recording density of the magnetic disk becomes higher, the size of a defect to be detected is decreasing, and the number of kinds of defects to be detected is increasing.

To address such demands, the patent document 1 describes that an image of regular-reflection light from the surface of the disk which is obliquely irradiated with a laser beam is detected by "n" pieces of light receiving elements arranged linearly, and the size of a recessed or projected defect in the surface of a substrate is detected with high precision on the basis of detection signal levels of the light receiving elements. However, it is not considered that a smaller defect in the surface of the substrate, for example, a shallow flaw defect (shallow defect) or a defect on the inside of the substrate is detected so as to be discriminated from the other defects.

The patent document 2 describes that a substrate is illuminated from multiple directions, regular-reflection light and scattering light from the substrate is detected, the state of a wave in the substrate itself or a local wave is determined from the waveform of the detection signals, and a defect is detected from the state. However, it is not described that a smaller defect in the surface of the substrate, for example, a shallow flaw defect (shallow defect) or a defect on the inside of the substrate is detected so as to be discriminated from the other defects.

The patent document 2 also describes that a mask is provided so that regular-reflection light does not enter a lens provided on the side of regular reflection from a substrate (disk) to thereby interrupt regular-reflection light other than scatting light, and that a half mirror is provided in place of a mask, and regular-reflection light is reflected by the half mirror and detected by a detector. However, it is not considered that a smaller defect in the surface of the substrate, for example, a shallow flaw defect (shallow defect) or a defect on the inside of the substrate is detected so as to be discriminated from the other defects by using detection signals of scattering light around the regular-reflection light excluding the regular-reflection light and a detection signal of the regular-reflection light.

SUMMARY

An object of the present invention is to address the problems and to provide an optical inspection apparatus for inspecting a magnetic disk, capable of detecting a smaller defect in the surface of a substrate, for example, a shallow flaw defect (shallow defect) or a defect on the inside of the substrate so as to be discriminated from the other defects.

To achieve the object, in the present invention, an optical inspection apparatus for detecting a defect in a surface of a sample is constructed by including: a stage which rotates a sample and continuously moves the sample in one direction; a light irradiator which irradiates a surface of the sample which is rotated and continuously moved in one direction by the stage, with illumination light which is incident in a direction obliquely to the surface of the sample; a first detector which detects an image of forward scattering light around an optical axis of regular-reflection light by using reflection light including the forward scattering light around the optical axis of the regular-reflection light while excluding the regular-reflection light from the surface of the sample irradiated with the illumination light from the light irradiator; a second detector which condenses and detects lateral scattering light which scatters laterally with respect to an incidence direction of the illumination light in the scattering light from the surface of the sample irradiated with the illumination light from the light irradiator; and a defect extractor which processes signals detected by the first and second detector to extract a defect including a scratch defect in an arbitrary direction in the surface of the sample.

To achieve the object, in the present invention, an optical inspection apparatus for detecting a defect in a surface of a sample is constructed by including: a stage which rotates a sample and continuously moves the sample in one direction; a light irradiator which irradiates a surface of the sample which is rotated and continuously moved in one direction by the stage, with illumination light which is incident in a direction obliquely to the surface of the sample; a first detector which detects regular-reflection light from the surface of the sample irradiated with the illumination light from the light irradiator; a second detector which condenses and detects lateral scattering light which scatters laterally with respect to an incidence direction of the illumination light in the scattering light from the surface of the sample irradiated with the illumination light from the light irradiator; and a defect extractor which processes signals detected by the first and second detector to extract a defect including a scratch defect in an arbitrary direction in the surface of the sample.

Further, to achieve the object, in the present invention, an optical inspection method of defecting a defect in a surface of a sample includes the steps of: irradiating a surface of a sample which is rotated and continuously moved in one direction with illumination light which is incident in a direction obliquely to the surface of the sample; detecting an image of forward scattering light around an optical axis of regular-reflection light by using reflection light including the forward scattering light around the optical axis of the regular-reflection light while excluding the regular-reflection light, from the surface of the sample irradiated with the illumination light; condensing and detecting lateral scattering light which scatters laterally with respect to an incidence direction of the illumination light, in the scattering light from the surface of the sample irradiated with the illumination light; and processing a signal obtained by detecting the forward scattering light around the optical axis of the regular-reflection light and a signal obtained by condensing and detecting the lateral scattering light to extract a defect including a scratch defect in an arbitrary direction in the surface of the sample.

Further, to achieve the object, an optical inspection method for detecting a defect in a surface of a sample includes the steps of: irradiating a surface of a sample which is rotated and continuously moved in one direction with illumination light which is incident in a direction obliquely to the surface of the sample; detecting regular-reflection light from the surface of the sample irradiated with the illumination light; condensing and detecting lateral scattering light which scatters laterally with respect to an incidence direction of the illumination light, in the scattering light from the surface of the sample irradiated with the illumination light; and processing a signal obtained by detecting the regular-reflection light and a signal obtained by condensing and detecting the lateral scattering light to extract a defect including a scratch defect in an arbitrary direction in the surface of the sample.

According to the present invention, at the time of detecting scattering light from a sample and classifying defects extracted, defect information included in forward scattering light around the optical axis of the regular-reflection light can be also used. Therefore, defects including a scratch defect (shallow defect) which is shallow in an arbitrary direction in a surface of a sample can be extracted.

These features and advantages of the invention will be apparent from the following more particular description of preferred embodiments of the invention, as illustrated in the accompanying drawings.

BRIEF DESCRIPTION OF THE DRAWINGS

FIG. 7 is a table showing the presence or absence of a detection signal in each of detection systems for each of defect kinds;

DESCRIPTION OF THE PREFERRED EMBODIMENTS

To improve performance of classifying defects, the present invention provides a technique of separately detecting regular-reflection light from a substrate irradiated with illumination light and scattering light around the optical axis of the regular-reflection light, detecting a defect on a surface of the substrate by using a detection signal of an image of the scattering light around the optical axis which is separately detected, or a detection signal of an image of the scattering light around the optical axis and a detection signal of the regular-reflection light, and a detection signal of lateral scattering light, and classifying the kind of the detected defect.

Embodiments of the present invention will be described below with reference to the drawings.

First Embodiment

The configuration of an optical magnetic disk inspection apparatus according to a first embodiment will be described with reference to FIGS. 1A to 10.

Figure 1A:
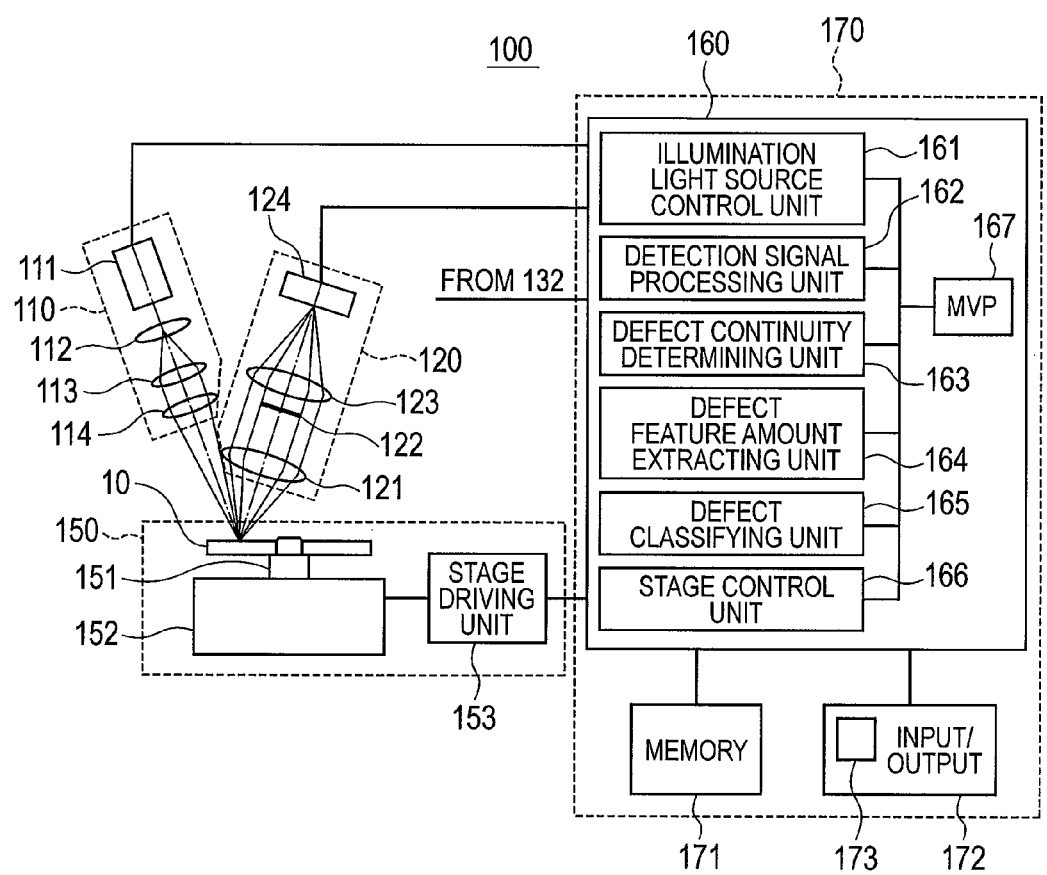
FIG. 1A is a block diagram showing a general schematic configuration of an optical inspection apparatus in a first embodiment.
Figure 1B:
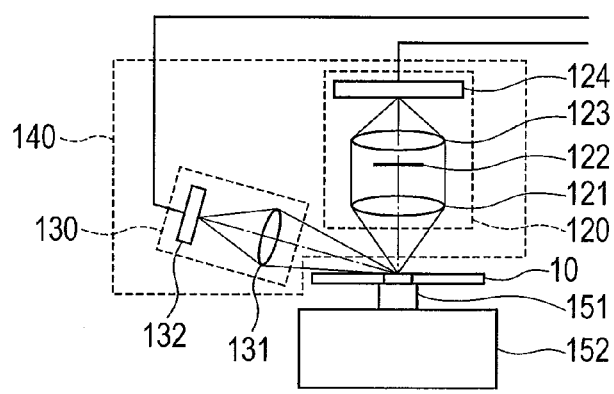
FIG. 1B is a side view of detection optics in the optical inspection apparatus in the first embodiment.

An optical magnetic disk inspection apparatus 100 according to the first embodiment has, as shown in FIGS. 1A and 1B, illumination optics 110, detection optics 140 configured to include regular-reflection light detection optics 120 and scattering light detection optics 130, a stage system 150, and a general control system 170.

The illumination optics 110 include a laser source 111, a beam expansion lens 112 expanding a laser beam emitted from the laser source 111, a collimate lens 113 converting the laser beam expanded by the beam expansion lens 112 to parallel rays, and a convergence lens 114 converging the parallel laser beams whose diameter is enlarged onto the surface of a sample 10.

The regular-reflection light detection optics 120 in the detection optics 140 are disposed along the optical axis of regular-reflection light from the sample 10 irradiated with the laser beam converged by the illumination optics 110, and include a condenser lens 121 for condensing reflection light including the regular-reflection light and the scattering light from the sample 10, a mask 122 for blocking the regular-reflection light from the sample 10 in the light which passed through the condenser lens 121, an image forming lens 123 for forming an image from reflection light (scattering light) from the sample 10 which is not blocked by the mask 122 at a predetermined magnification, and a detector 124 for detecting the image of the reflection light (scattering light) from the sample 10, which is formed by the image forming lens 123. By using an aspheric lens as the condenser lens 121, an optical system having a larger NA (numerical aperture) can be constructed, and defect detection sensitivity can be increased. The image forming lens 123 can be also constructed by an aspheric lens. The detector 124 is an array sensor formed by arranging plural detection elements in an array.

On the other hand, the scattering light detection optics 130 in the detection optics 140 include a condenser lens 131 for condensing lateral scattering light from the sample 10 which is irradiated with a laser beam and a detector 132 for detecting the scattering light condensed by the condenser lens 131.

The stage system 150 includes a rotatable spindle shaft 151 on which the sample 10 is placed, a stage 152 for moving the spindle shaft 151 in one direction in a plane, and a stage driving unit 153 for driving the spindle shaft 151 and the stage 152.

The general control system 170 has a signal process/control system 160, a memory 171 that stores inspection data and data of inspection parameters, and an input/output unit 172 having a display screen 173.

The signal process/control system 160 includes: an illumination light source control unit 161 for controlling the laser source 111 of the illumination optics 110; a detection signal processing unit 162 for receiving output signals of the detector 124 of the regular-reflection light detection optics 120 and the detector 132 of the scattering light detection optics 130, amplifying them, A/D converting the signals to digital signals, and performing signal process on the digital signals to detect a defect candidate; a defect continuity determining unit 163 for extracting a continuous defect in the sample 10 by using the information of the defect candidate detected by the detection signal processing unit 162, the information of rotation of the spindle shaft 151, and the information of the position of the stage 152; a defect feature amount extracting unit 164 for extracting a feature amount of the defect detected by the detection signal processing unit 162 including the continuous defect extracted by the defect continuity determining unit 163; a defect classifying unit 165 for classifying a defect by using the information of the feature amount of the defect extracted by the defect feature amount extracting unit 164; a stage control unit 166 for controlling the operation of the spindle shaft 151 and the stage 152 by controlling the stage driving unit 153; and an MUP 167 for controlling the illumination light source control unit 161, the detection signal processing unit 162, the defect continuity determining unit 163, the defect feature amount extracting unit 164, the defect classifying unit 165, and the stage control unit 166.

Figure 1C:
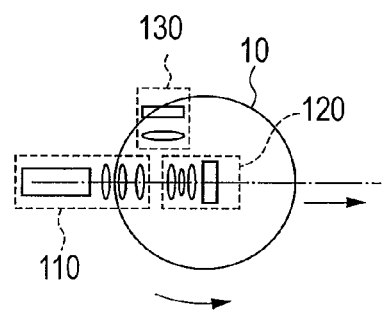
FIG. 1C is a plan view of the detection optics in the optical inspection apparatus in the first embodiment.

The illumination optics 110, the regular-reflection light detection optics 120, and the scattering light detection optics 130 are disposed in the relations with respect to the sample 10 as shown in the plan view of FIG. 1C. The arrows in FIG. 1C indicate the direction of rotation and the direction of linear movement of the substrate 10.

Figure 2:
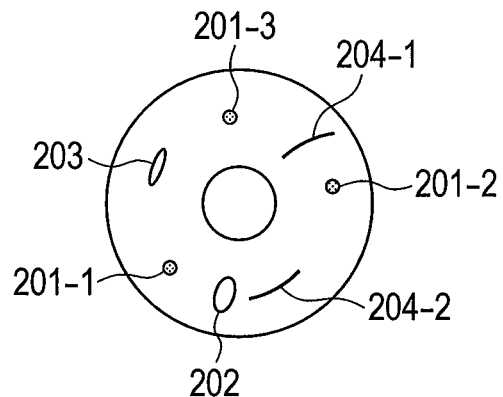
FIG. 2 is a plan view showing a state of defects in a magnetic disk to be inspected.

Defects in the sample 10 are detected by the optical magnetic disk inspection apparatus 100 having the above-described configuration. FIG. 2 illustrates an example of defects on the sample 10 to be inspected.

FIG. 2 is a plan view of a magnetic disk as the sample 10 to be inspected. In the magnetic disk as the sample 10, thin films in multiple layers including a magnetic film layer are formed on the surface by various manufacturing processes. By the various manufacturing processes, various defects are caused. In many cases, foreign matters 201-1 to 201-3 adhered to the surface of the sample 10 do not cause a problem because they are washed out by cleaning before the sample 10 is assembled in a hard disk drive. On the other hand, each of a bump defect 202 as an expansion of the surface of the sample 10, a pit defect 203 as a recess in the surface, and the like is often a gentle defect which spreads thinly (a few nm to tens nm) in a large area (1 mm$^2$) in the surface of the sample 10. Those defects do not cause a problem when the sample 10 is assembled in a hard disk drive to make a magnetic head float by high-speed rotation. However, they may become a cause of a change in the thickness of a recording layer which is formed in a deposition process.

Scratches 204-1 and 204-2 are defects which occur when an abrading agent comes off from an abrasive pad and have a shape such as a long streaky shape or a short flaw, in which a recess and a projection are mixed. The defect having such a sharp projection may interfere with a magnetic head when the sample 10 is assembled in a hard disk drive to make the magnetic head float by high-speed rotation. The defect may cause a critical failure in the hard disk drive. It is therefore important to inspect the sample (magnetic disk) 10 before assembly to the hard disk drive to detect those defects and to prevent the sample 10 having a defect as a defective from being passed to the next process.

Figure 3A:
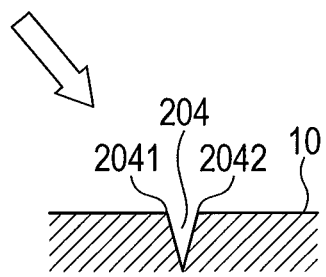
FIG. 3A is a section of a magnetic disk to be inspected, having a scratch defect.
Figure 3B:
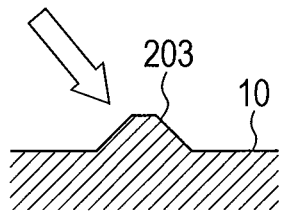
FIG. 3B is a section of a magnetic disk to be inspected, having a projected defect.

FIG. 3A is a cross section of the sample 10 in a region having the scratch defect 204 in the surface. FIG. 3B is a cross section of the sample 10 in a region having the bump defect 203 as a projection in the sample surface.

In the case where light falls on the scratch defect 204 shown in FIG. 3A from the direction of the arrow, relatively strong scattering light is generated from edge portions 2041 and 2042. The scattering light has a characteristic such that it is generated relatively weak in the longitudinal direction of the scratch defect 204 (the direction perpendicular to the drawing sheet of FIG. 3A) and relatively strong in the direction orthogonal to the longitudinal direction. When light is emitted along the longitudinal direction of the scratch defect 204, relatively strong scattering light is generated in the longitudinal direction but the strength of the scattering light in the direction orthogonal to the longitudinal direction of the scratch defect 204 is relatively weak. That is, in the example of the sample 10 shown in FIG. 2, in the case of illuminating the sample 10 by the illumination optics 110 shown in FIG. 1 (in FIG. 2, illuminated along the radial direction of the sample 10), relatively strong reflection light is generated in the radial direction of the sample 10 from the scratch 204-1 which is long in the radial direction and the scratch 204-2 which is long in the circumferential direction. On the other hand, the strength of scattering light which is generated in the circumferential direction is relatively low. That is, in the case of detecting the scratch defect 204 by the scattering light detection optics 130, the directivity is higher than that in the case of detecting a defect of another shape.

On the other hand, in the direction of the regular-reflection light generated from the sample 10 illuminated by the illumination optics 110, almost constant reflection light (including the regular-reflection light and scattering light) is generated regardless of the directions of the scratches 204-1 and 204-2. Although the regular-reflection light from the sample 10 is also generated from a part having no defect, scattering light is generated from a part having a defect. Consequently, by detecting scattering light separately from the regular-reflection light, the scratch defect 204 can be always detected regardless of the orientation of the scratch defect 204.

Therefore, by disposing the detector in the direction of the regular-reflection light and blocking the regular-reflection light to incident in the detector and detect an image of the scattering light generated from the scratch 204-1 or 204-2, the defect can be detected regardless of the orientation of the scratch 204-1 or 204-2. It is particularly effective to detect a shallow scratch defect (shallow defect).

The regular-reflection light detection optics 120 of FIG. 1A are constructed in consideration of the above mentioned idea. By blocking the regular-reflection light from the sample 10 by the mask 122 and forming an image of scattering light generated around the optical axis of the regular-reflection light by the image forming lens 123 on the detector 124, the scratch 204 in the sample 10 can be detected without overlooking.

Figure 4A:
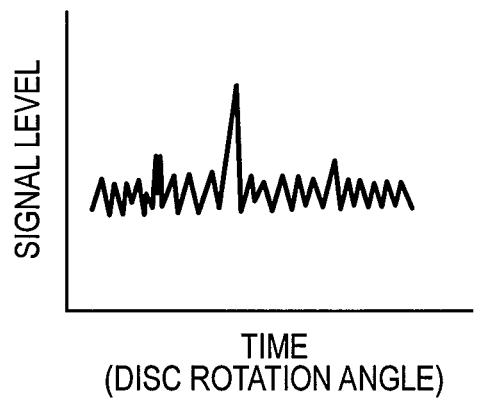
FIG. 4A is a detection signal having a noise, which is obtained when the surface of a magnetic disk having a defect is inspected.
Figure 4B:
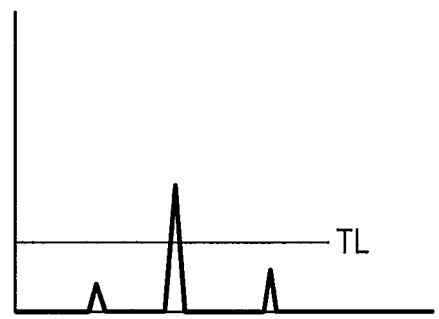
FIG. 4B is a detection signal which is obtained when the surface of a magnetic disk having a defect is inspected and from which noise is eliminated.

FIG. 4A shows an example of a detection signal from the detector 124 or 132. The detection signal from the detector 124 or 132 includes a defect signal in a state where it is buried in a noise signal. By cutting off the signals equal to or less than a predetermined level in the detection signal as noises, a signal as shown in FIG. 4B is obtained. A threshold value (TL) is set for the signal, a signal exceeding the threshold value is extracted as a defect signal, and information of an inspection position on the sample 10 corresponding to the extracted defect signal is obtained, from the stage driving unit 153 via the stage control unit 166. And the obtained information is supplied as the position information of the defect to the detection signal processing unit 162.

Figure 5:
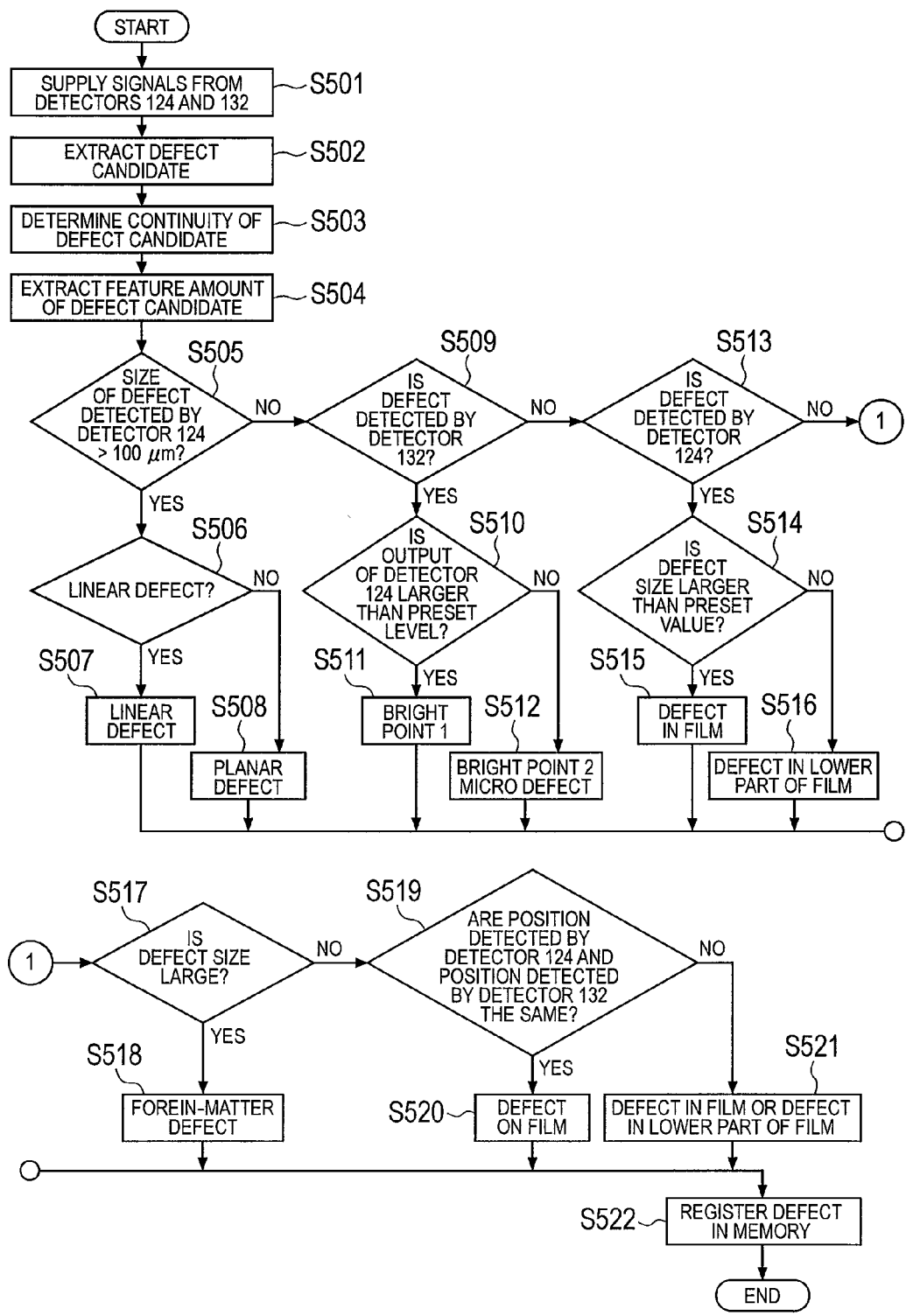
FIG. 5 is a flowchart of processes for detecting and classifying a defect in the first embodiment.

Next, the flow of processes executed by the signal process/control system 160 to detect a defect in the sample 10 on the basis of the above-described idea by using the inspection apparatus shown in FIGS. 1A and 1B will be described with reference to FIG. 5.

First, the spindle shaft 151 and the stage 152 are driven by the stage driving unit 153 which is controlled by the stage control unit 166 in a state where the sample 10 is placed on the spindle shaft 151 to continuously move the sample 10 in one direction while rotating the sample 10. In this state, the laser source 111 of the illumination optics 110 is driven by the illumination light source control unit 161 to emit a laser beam to the sample 10. Reflection light from the sample 10 irradiated with the laser beam is detected by the regular-reflection light detection optics 120 and the scattering light detection optics 130, and detection signals from the detectors 124 and 132 are supplied to the detection signal processing unit 162 (S501).

The detection signal processing unit 162, to which the detection signals from the detectors 124 and 132 are supplied, amplifies each of the input signals, A/D converts the amplified signals to digital signals, processes the digital signals, and checks them with each other to extract a defect candidate (S502).

The information of the extracted defect candidate is sent to the defect continuity determining unit 163, continuity of the defect is determined by using the information of the rotation of the spindle shaft 151 and the information of the position of the stage 152 obtained from the stage control unit 166 (S503), and a scratch defect is extracted.

The digital signals based on the signals from the detectors 124 and 132 are also sent to the defect feature amount extracting unit 164 where feature amounts (shape, size, and the like) of the defect are extracted (S504).

The information of the extracted feature amounts of the defect is sent to the defect classifying unit 165 and subjected to defect classifying process. In the defect classifying process, the size of defect which is extracted by the defect feature amount extracting unit 164 is judged whether the size is 100 µm or larger from the signal obtained from the detector 124 of the regular-reflection light detection optics 120 (S505). In the case the defect has a size of 100 µm or more, the defect is determined whether or not the defect is a linear defect by using the result of the process of S503 (S506). If YES, the defect is determined as a linear defect (S507). On the other hand, in the case where the defect is not determined as a linear defect in S506, the defect is determined as a planar defect caused by contamination (S508).

For the defect determined that its size is not equal to or larger than 100 µm in S505, it is judged from an output signal of the detector 132 whether or not a detection signal corresponding to the defect is also detected by the scattering light detection optics 130 (S509). In the case where it is determined that the signal is not detected by the scattering light detection optics 130, the size of the signal obtained from the detector 124 of the regular-reflection light detection optics 120 is compared with a preset level (S510). When the case where the size is larger than the preset level, the defect is determined as a large bright point (S511). When the size is equal to or less than the preset level, the defect is determined as a small bright point (micro defect) (S512).

In the case where it is determined in S509 that the signal is detected by the scattering light detection optics 130, it is judged whether or not the defect is also detected by the regular-reflection light detection optics 120 (S513). When the defect is not detected by the regular-reflection light detection optics 120, the size of the defect is compared with a preset value (S514). In the case where the size of the defect is larger than the preset value, the defect is determined as a defect (defect existing inside the film) existing in the sample 10 (in a thin film formed on the surface of the sample 10) (S515). In the case where the size is equal to or less than the preset value, the defect is determined as a defect (defect existing under the film) under the thin film formed on the surface of the sample 10 (S516).

In the case where the defect is also detected by the regular-reflection light detection optics 120, the size of the defect is compared with a preset value (S517). When the size of the defect is larger than the preset value, the defect is determined as a foreign-matter defect (S518). When the size is equal to or less than the preset value, the position on the sample 10 determined from the signal detected by the regular-reflection light detection optics 120 and the position on the sample 10 determined from the signal detected by the scattering light detection optics 130 are compared with each other (S519). When the positions are the same, the defect is determined as a defect on the surface of the sample 10 (S520). When the positions are not the same, the defect is determined as a defect in/below the thin film formed on the surface of the sample 10 (S521).

The information of each of the defects classified as described above is recorded and stored in the memory 171.

As described above, by detecting and classifying a defect by using the information of scattering light of a part around the optical axis of the regular-reflection light obtained from the detection signal of the regular-reflection light detection optics 120 and the information of lateral scattering light obtained from the detection signal of the scattering light detection optics 130, the detected defect can be classified more finely.

Second Embodiment

A second embodiment of the present invention will now be described with reference to FIGS. 6A and 6B.

Figure 6A:
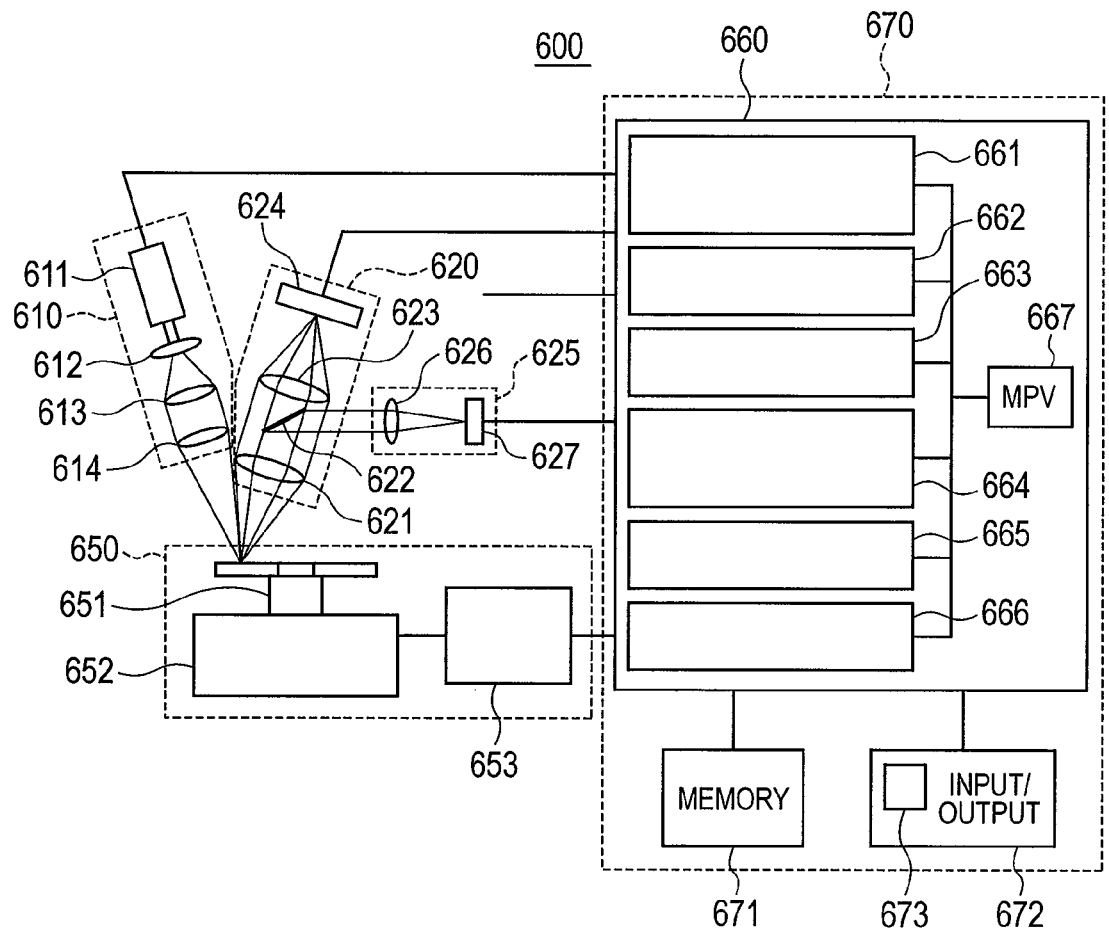
FIG. 6A is a block diagram showing a general schematic configuration of an optical inspection apparatus in a second embodiment.

In the embodiment, the mask 122 in the regular-reflection light detection optics 120 of the inspection apparatus shown in FIG. 1 is replaced by a reflecting mirror 622 as shown in FIG. 6A to detect the regular-reflection light. That is, for detection and classification of a defect, information of the regular-reflection light from the sample 10 is also used.

A magnetic disk inspection apparatus 600 in the second embodiment shown in FIGS. 6A and 6B has, is similar to the configuration of the inspection apparatus 100 in the first embodiment described with reference to FIGS. 1A to 1C. The magnetic disk inspection apparatus 600 includes illumination optics 610, detection optics 640 including regular-reflection light detection optics 620 and scattering light detection optics 630, a stage system 650, and a general control system 670. The configuration is basically similar to that of FIG. 1A except that the mask 122 of the regular-reflection light detection optics 120 is replaced with the reflecting mirror 622 as shown in FIG. 6A and a regular-reflection-light detection system 625 having a condenser lens 626 and a detector 627 is newly provided. Consequently, detailed description of the configuration will be omitted.

The magnetic disk inspection apparatus 600 can also use the information of the regular-reflection light for classification of a defect, so that the precision of the classification can be further improved. FIG. 7 is a table showing the relations between the lateral scattering light detection signal, the regular-reflection light detection signal, and a defect kind. By using the regular-reflection light detection signal, a shallow defect (a shallow defect among scratch defects) can be detected.

Figure 8:
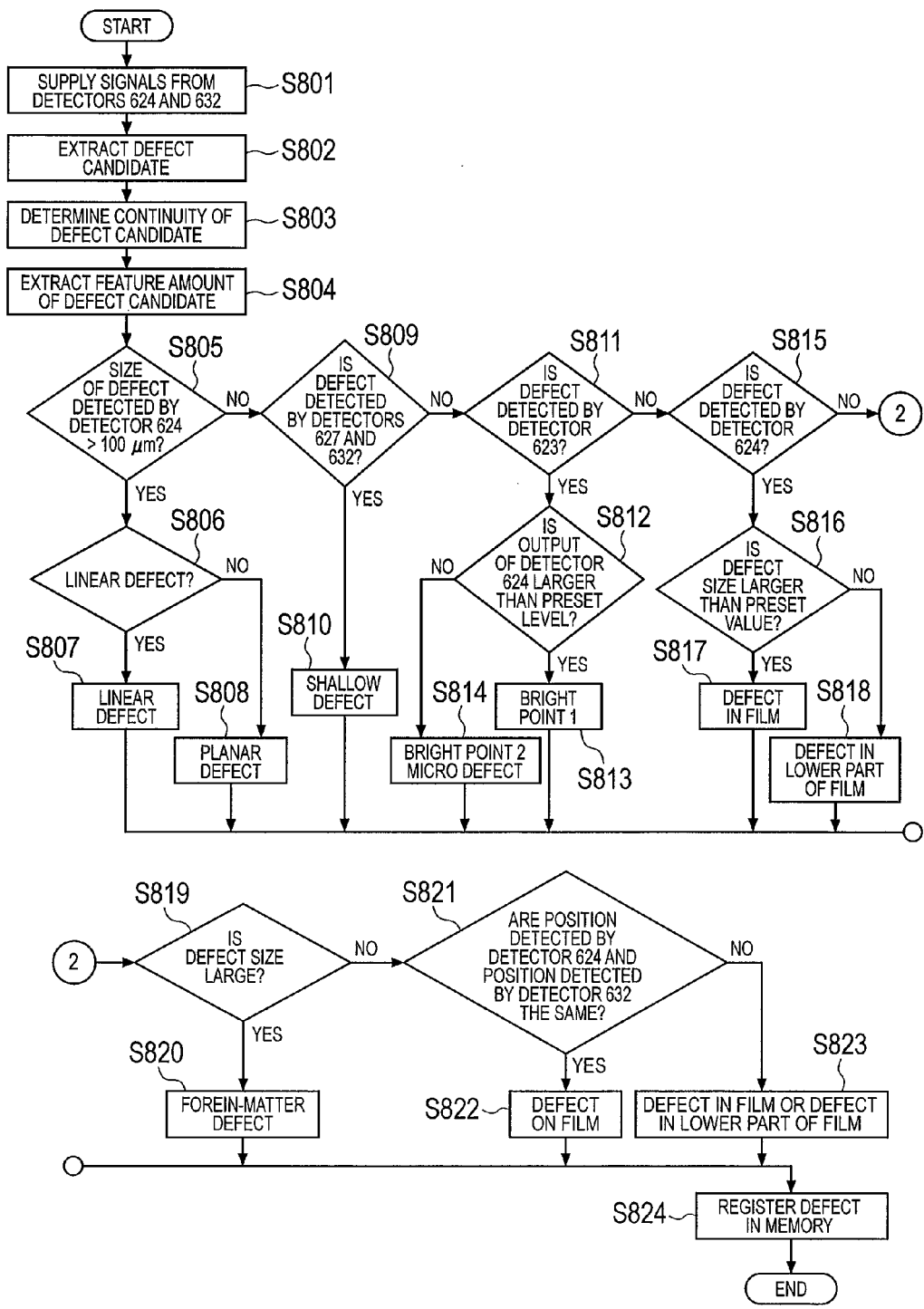
FIG. 8 is a flowchart of processes for detecting and classifying a defect in the second embodiment.

Next, the flow of processes of detecting/classifying a defect in the magnetic disk inspection apparatus 600 will be described with reference to FIG. 8.

Figure 6B:
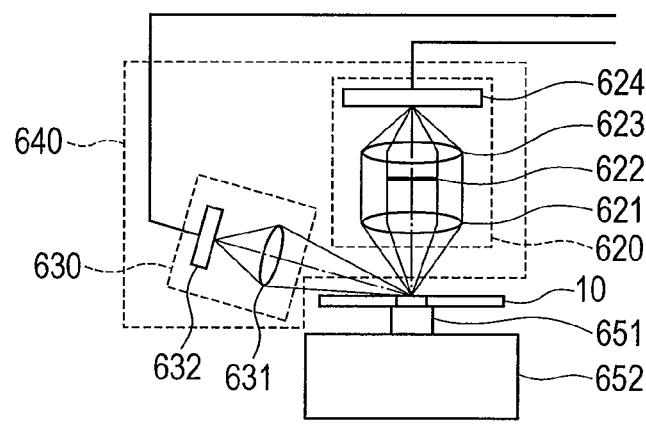
FIG. 6B is a side view of detection optics in the optical inspection apparatus in the second embodiment.

First, reflection light from the sample 10 irradiated with a laser beam in a state where the sample 10 is moved in one direction while being rotated is detected by the regular-reflection light detection optics 620 and the scattering light detection optics 620 as illustrated in FIG. 6B, and detection signals from detectors 624 and 632 are supplied to a detection signal processing unit 662 (S801).

The detection signal processing unit 662, to which the detection signals from the detectors 624 and 632 are supplied by amplifying and converting from analog signals to digital signals, processes the digital signals, and checks them with each other to extract a defect candidate (S802).

The information of the extracted defect candidate is sent to a defect continuity determining unit 663 where continuity of the defect is determined by using the information of the rotation of a spindle shaft 651 and the information of the position of a stage 652 obtained from a stage control unit 666 (S803), and a scratch defect is extracted.

The digital signals based on the signals from the detectors 624 and 632 are also sent to a defect feature amount extracting unit 664 where feature amounts (shape, size, and the like) of the defect are extracted (S804).

The information of the extracted feature amounts of the defect is sent to a defect classifying unit 665 and subjected to defect classifying process. In the defect classifying process, the size of defect which is extracted by the defect feature amount extracting unit 664 is judged whether the size is 100 μm or larger from the signal obtained from the detector 624 of the regular-reflection light detection optics 620 (S805). In the case the defect has a size of 100 μm or more, the defect is determined whether or not the defect is a linear defect by using the result of the process of S803 (S806). If YES, the defect is determined as a linear defect (S807). On the other hand, in the case where the defect is not determined as a linear defect in S806, the defect is determined as a planar defect caused by contamination (S808).

For the defect determined that its size is not equal to or larger than 100 μm in S805, it is judged from an output signal of the detector 632 whether or not a detection signal corresponding to the defect is also detected by the scattering light detection optics 625 and also is checked if the defect is not detected by the scattering light detection optics 630 (S809). If YES, that is, in the case where the signal is detected by the regular-reflection light detection optics 625 and is not detected by the scattering light detection optics 630, the defect is determined as a shallow defect (S810).

On the other hand, in the case where NO is determined in S809, it is checked whether or not the detection signal corresponding to the defect is also detected by the scattering light detection optics 630 from the output signal of the detector 632 (S811). When it is found that the signal is not detected by the scattering light detection optics 630, the size of the signal obtained from the detector 624 of the regular-reflection light detection optics 620 is compared with a preset level (S812). In case the size is larger than the preset level, the defect is determined as a large bright point (S813). In case the size is equal to or less than the preset level, the defect is determined as a small bright point (micro defect) (S814).

In the case where it is determined in S811 that the signal is detected by the scattering light detection optics 130, it is determined whether or not the defect is also detected by the regular-reflection light detection optics 620 (S815). When the defect is not detected by the regular-reflection light detection optics 620, the size of the defect is compared with a preset value (S816). In the case where the size of the defect is larger than the preset value, the defect is determined as a defect (defect existing inside the film) existing in the sample 10 (in a thin film formed on the surface of the sample 10) (S817). In the case where the size is equal to or less than the present value, the defect is determined as a defect (defect existing under the film) existing under the thin film formed on the surface of the sample 10 (S818).

When it is determined in S815 that the defect is also detected by the regular-reflection-light detection optics 620, the size of the defect is compared with a preset value (S819). When the size of the defect is larger than the preset value, the defect is determined as a foreign-matter defect (S820). When the size is equal to or less than the preset value, the position on the sample 10 determined from the signal detected by the regular-reflection light detection optics 620 and the position on the sample 10 determined from the signal detected by the scattering light detection optics 630 are compared with each other (S821). When the positions are the same, the defect is determined as a defect on the surface of the sample 10 (S822).

When the positions are not the same, the defect is determined as a defect in/below the thin film formed on the surface of the sample 10 (S823).

The information of each of the defects classified as described above is recorded and stored in a memory 671.

As described above, by detecting and classifying a defect by using the information of scattering light of a part around the optical axis of the regular-reflection light obtained from the detection signals of the regular-reflection light detection system 625 and the regular-reflection light detection optics 620 and the information of lateral scattering light obtained from the detection signal of the scattering light detection optics 630, the detected defect can be classified more finely.

Third Embodiment

Figure 9:
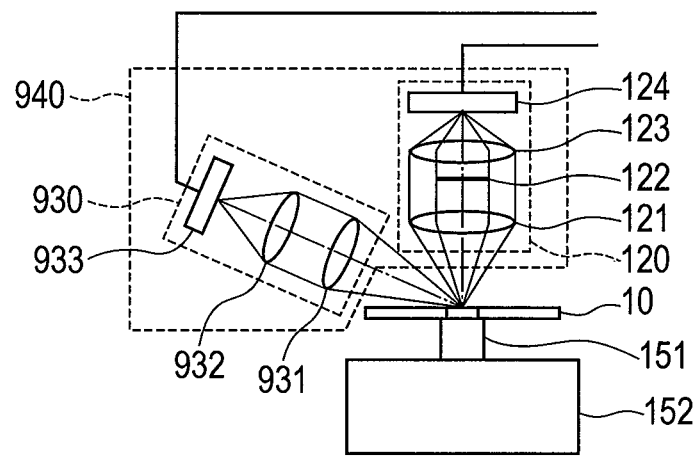
FIG. 9 is a side view of detection optics in an optical inspection apparatus in a third embodiment.

In a third embodiment, an example of constructing the scattering light detection optics 130 of the magnetic disk inspection apparatus 100 described in the first embodiment by image formation optics as shown in FIG. 9 will be described.

The configuration of a magnetic disk inspection apparatus in the third embodiment is similar to that of the magnetic disk inspection apparatus 100 described in the first embodiment except for the point that the scattering light detection optics 130 are constructed by image formation optics as shown in FIG. 9.

FIG. 9 is a side view of a detection optics 940 including a scattering light detection optics 930 of the third embodiment and the regular-reflection light detection optics 120 in the first embodiment.

The scattering light detection optics 930 include a condenser lens 931 for condensing scattering light from the sample 10 irradiated with a laser beam, an image forming lens 932 for forming an image of the scattering light from the sample 10 condensed by the condenser lens 931, and a detector 933 for detecting the image of the scattering light formed by the image forming lens 932.

Since the configuration other than the detection optics 940 in the third embodiment is substantially the same as that described in the first embodiment, description will be given by applying the configuration of FIG. 1.

In the third embodiment, an optical image is detected by both the detectors 124 and 933. Consequently, the detection signal processing unit 162 adjusts positions of the pixels in each of the images obtained by the detectors and, after that, detects a defect from the images whose positions are adjusted. The defect feature amount extracting unit 164 extracts feature amounts of a defect from each of the images whose positions are adjusted. Further, the defect classifying unit 165 classifies the defect by using the information of the feature amounts of the defects in the images extracted by the defect feature amount extracting unit 164.

Figure 10:
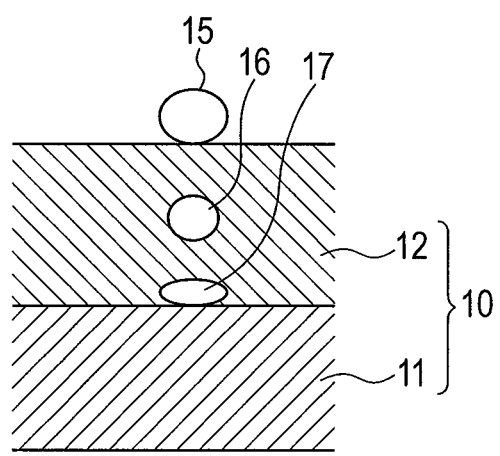
FIG. 10 is a sectional view of a magnetic disk showing an example of small defects existing on a thin film and in a middle part and in a lower part of the thin film formed on the surface of a magnetic disk.

By constructing the scattering light detection optics with the image forming optics as described above, defects on the sample are detected discriminately from a detected image. For example, as shown in FIG. 10, a defect 15 existing on the surface of a thin film layer 12 (in FIG. 10, simply shown as a single layer) formed on a substrate 11 of the sample 10, a defect 16 existing in the thin film layer 12, and a defect 17 existing in a lower part of the thin film layer 12 can be detected discriminately from one another.

In the third embodiment, a defect is detected and classified by using an image obtained by the regular-reflection light detection optics and an image obtained by the scattering light detection optics, so that higher-precision defect detection and higher-reliability defect classification can be performed.

Fourth Embodiment

In the foregoing first to third embodiments, at least the regular-reflection light detection optics is constructed by the image forming optics. In a fourth embodiment, regular-reflection light from a sample is detected without using the image forming optics.

Figure 11A:
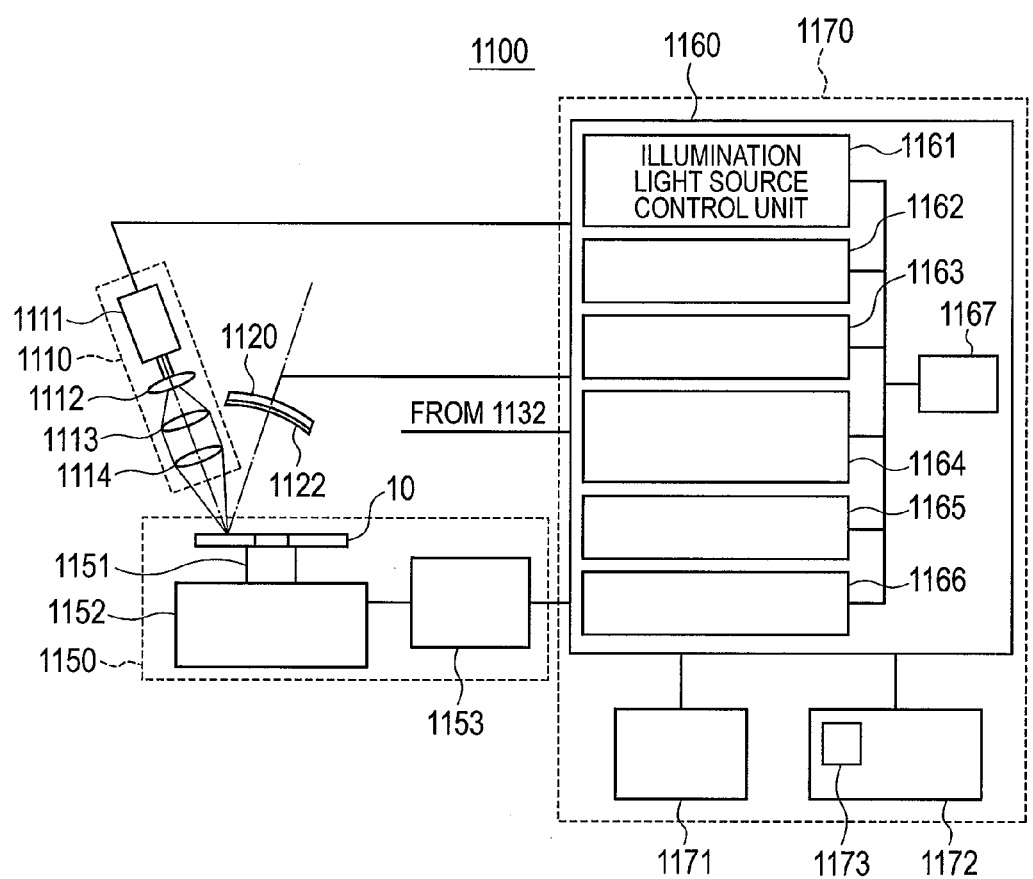
FIG. 11A is a block diagram showing a general schematic configuration of an optical inspection apparatus in a fourth embodiment.
Figure 11B:
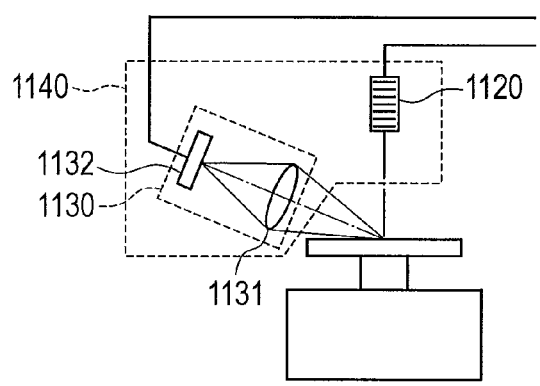
FIG. 11B is a side view of detection optics in the optical inspection apparatus in the fourth embodiment.
Figure 11C:
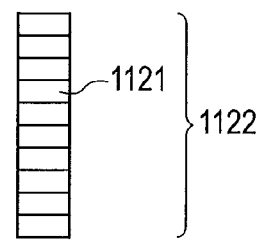
FIG. 11C is a front view of a one-dimensional sensor array of the optical inspection apparatus in the fourth embodiment.

FIGS. 11A to 11C show the configuration of an optical magnetic disk inspection apparatus 1100 in the fourth embodiment.

As shown in FIG. 11A, the magnetic disk inspection apparatus 1100 has illumination optics 1110, detection optics 1140 configured to include regular-reflection light detection optics 1120 and scattering light detection optics 1130, a stage system 1150, and a general control system 1170.

In a manner similar to the case of the first embodiment, the illumination optics 1110 include a laser source 1111, a beam expansion lens 1112 expanding a laser beam emitted from the laser source 1111, a collimate lens 1113 converting the laser beam expanded by the beam expansion lens 1112 to parallel rays, and a convergence lens 1114 converging the parallel laser beams whose diameter is enlarged onto the surface of the sample 10.

As shown in FIG. 11C, the regular-reflection light detection optics 1120 in the detection optics 1140 is constructed by a one-dimensional array sensor 1122 formed by disposing plural photo diode elements 1121 in an array.

On the other hand, as shown in FIG. 11B, the scattering light detection optics 1130 in the detection optics 1140 include a condenser lens 1131 for condensing lateral scattering light from the sample 10 which is irradiated with a laser beam and a detector 1132 for detecting the scattering light condensed by the condenser lens 1131.

The stage system 1150 includes a rotatable spindle shaft 1151 on which the sample 10 is placed, a stage 1152 for moving the spindle shaft 1151 in one direction in a plane, and a stage driving unit 1153 for driving the spindle shaft 1151 and the stage 1152.

The general control system 1170 has a signal process/control system 1160, a memory 1171 that stores inspection data and data of inspection parameters, and an input/output unit 1172 having a display screen 1173.

The signal process/control system 1160 includes: an illumination light source control unit 1161 for controlling the laser source 1111 of the illumination optics 1110; a detection signal processing unit 1162 for receiving output signals of the array sensor 1122 of the regular-reflection light detection optics 1120 and the detector 1132 of the scattering light detection optics 1130, amplifying them, A/D converting the signals to digital signals, and performing signal process on the digital signals to detect a defect candidate; a defect continuity determining unit 1163 for extracting a continuous defect in the sample 10 by using the information of the defect candidate detected by the detection signal processing unit 1162, the information of rotation of the spindle shaft 1151, and the information of the position of the stage 1152; a defect feature amount extracting unit 1164 for extracting a feature amount of the defect detected by the detection signal processing unit 1162 including the continuous defect extracted by the defect continuity determining unit 1163; a defect classifying unit 1165 for classifying a defect by using the information of the feature amount of the defect extracted by the defect feature amount extracting unit 1164; a stage control unit 1166 for controlling the operation of the spindle shaft 1151 and the stage 1152 by controlling the stage driving unit 1153; and an MUP 1167 for controlling the illumination light source control unit 1161, the detection signal processing unit 1162, the defect continuity determining unit 1163, the defect feature amount extracting unit 1164, the defect classifying unit 1165, and the stage control unit 1166.

As shown in FIG. 11A, the regular-reflection light detection system 1120 of the detection optics 1140 has a configuration to directly detect regular-reflection light from the sample 10 by the one-dimensional array sensor 1122 without using a lens system.

FIGS. 12A and 12B and FIGS. 13A and 13B show an example of outputs from the photodiode elements (pixels) 1121 constructing the one-dimensional array sensor 1122 when regular-reflection light from the sample 10 is detected by the regular-reflection light detection optics 1120.

Figure 12A:
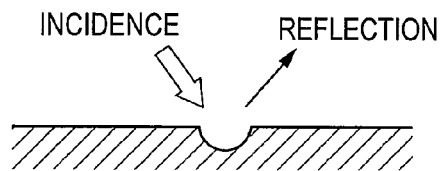
FIG. 12A is a cross section of a substrate of a part having a recessed defect.
Figure 12B:
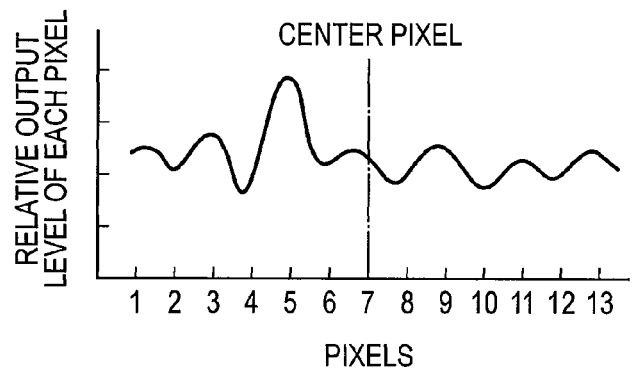
FIG. 12B is a graph showing an example of output waveform from photo diode elements (pixels) of the one-dimensional sensor array when reflection light from the part having the recessed defect is detected by the one-dimensional sensor array.

FIG. 12B shows an example of outputs from the photodiode elements (pixels) 1121 when illumination light is emitted from the direction of the arrow to the recessed defect shown in FIG. 12A and regular-reflection light which is reflected from the sample 10 in the direction of the arrow by the illumination of the illumination light is detected by the one-dimensional array sensor 1122. There is a characteristic such that, in the case where regular-reflection light from a surface having no defect (normal face) of the sample 10 is received, outputs from the elements 1121 of the one-dimensional array sensor 1122 forms a waveform corresponding to a uniform distribution of the wavefront strength of the regular-reflection light. On the other hand, in the case where reflection light from a region including a recessed defect is detected by the photodiode elements (pixels) 1121 of the one-dimensional array sensor 1122, the peak level of signals output from photodiode elements (pixels) which detects regular-reflection light from the recessed defect is higher than a level of signals output from photodiode elements (pixels) which detects regular-reflection light from in the periphery of the recessed defect (the case of FIG. 12B shows an output of the fifth photodiode element (pixel) 1121) which detects regular-reflection light from the recess defect shown in FIG. 12A).

Figure 13A:
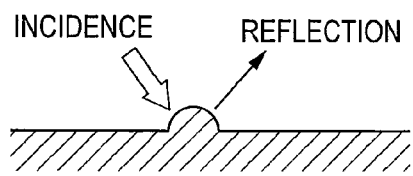
FIG. 13A is a cross section of a substrate of a part having a projected defect.
Figure 13B:
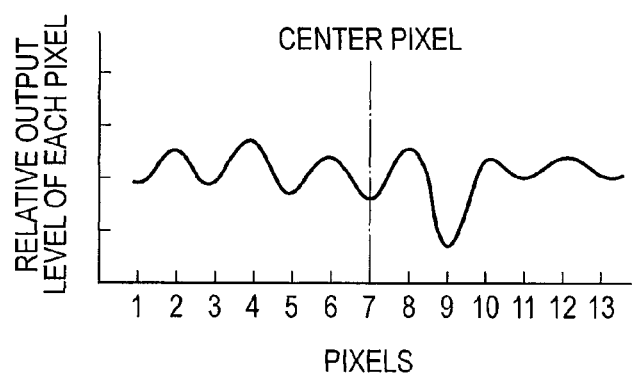
FIG. 13B is a graph showing an example of output waveform from photo diode elements (pixels) of the one-dimensional sensor array when reflection light from the part having the projected defect is detected by the one-dimensional sensor array.

On the other hand, FIG. 13B shows an example of outputs from the photodiode elements (pixels) 1121 when illumination light emitted from the direction of the arrow to a projected defect shown in FIG. 13A and regular-reflected in the direction of the arrow is detected by the one-dimensional array sensor 1122. There is a characteristic such that, in the case where regular-reflection light from the projected defect part is detected by the one-dimensional array sensor 1122, the detection level of the photodiode element (pixel) 1121 which detects regular-reflection light from a region including the projected defect becomes lower than the regular-reflection light detection level of the photodiode element (pixel) which detects regular-reflection light from a region in the periphery of the projected defect (the case of FIG. 13B shows an output of the ninth photodiode element (pixel) 1121) which detects regular-reflection light from the projected defect shown in FIG. 13A).

In such a manner, the position and the kind of a defect can be specified from the characteristics of the changes in the output signal level from the photodiode elements (pixels) 1121 of the one-dimensional array sensor 1122. Since the detection signal of the regular-reflection light and the detection signal of the scattering light can be distinguished from the level of the signal detected by each of the photodiode elements (pixels) 1121 of the one-dimensional array sensor 1122, a continuous defect such as a scratch defect can be classified by a method similar to that described in the second embodiment.

Modification of Fourth Embodiment

Figure 14A:
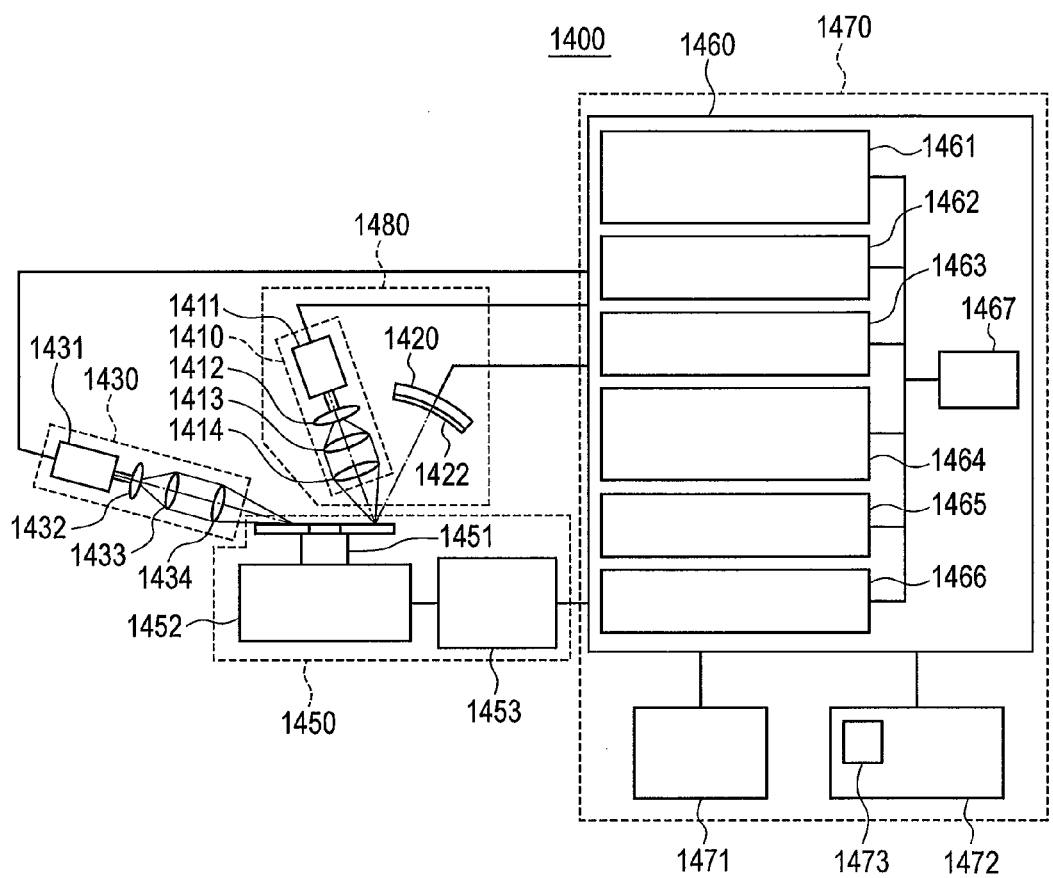
FIG. 14A is a block diagram showing a general schematic configuration of an optical inspection apparatus in a modification of the fourth embodiment.
Figure 14B:
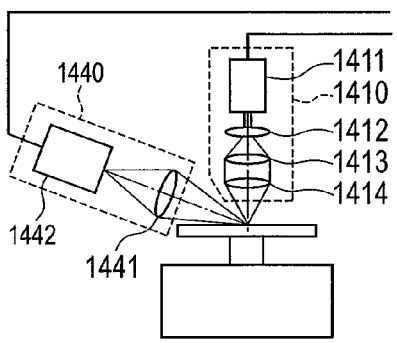
FIG. 14B is a side view of detection optics in the optical inspection apparatus in the modification of the fourth embodiment.
Figure 14C:
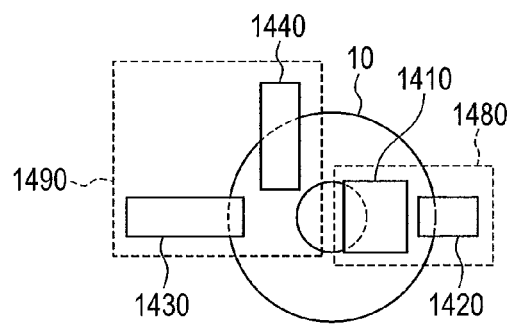
FIG. 14C is a plan view of the detection optics of the optical inspection apparatus in the modification of the fourth embodiment.

FIGS. 14A to 14C show an example of an optical disk inspection apparatus 1400 in which the regular-reflection-light detection optics and the lateral scattering light detection optics are constructed separately from each other.

As shown in FIG. 14C, the optical systems in the modification are separated as regular-reflection light detection optics 1480 and scattering light detection optics 1490. A right-side part in the rotating sample 10 is inspected by the regular-reflection light detection optics 1480 and a left-side part is inspected by the scattering light detection optics 1490. By presetting the positional relations on the sample 10 inspected by the regular-reflection light detection optics 1480 and the scattering light detection optics 1490, the positions on the sample 10 of a defect detected by the regular-reflection light detection optics 1480 and a defect detected by the scattering light detection optics 1490 can be made correspond to each other.

The configuration of the optical magnetic disk inspection apparatus 1400 shown in FIG. 14A of the modification is substantially the same as that of the magnetic disk inspection apparatus 1100 described with reference to FIGS. 11A to 11C except for the point that the scattering light detection optics 1490 is provided. Specifically, the optical magnetic disk inspection apparatus 1400 has regular-reflection light detection optics 1480 including high-angle illumination optics 1410 and regular-reflection light detection optics 1420, scattering light detection optics 1490 including low-angle illumination optics 1430 and lateral scattering light detection optics 1440, a stage system 1450, and a general control system 1470.

In a manner similar to the case of the fourth embodiment, the high-angle illumination optics 1410 in the regular-reflection light detection optics 1480 have a laser source 1411, a beam expansion lens 1412 expanding a laser beam emitted from the laser source 1411, a collimate lens 1413 converting the laser beam expanded by the beam expansion lens 1412 to parallel rays, and a convergence lens 1414 converging the parallel laser beams whose diameter is enlarged onto the surface of the sample 10. The regular-reflection light detection optics 1420 are constructed by a one-dimensional array sensor 1422 formed by disposing a plurality of photodiode elements in an array in a manner similar to that shown in FIG. 11C.

On the other hand, like the high-angle illumination optics 1410, the low-angle illumination optics 1430 in the scattering light detection optics 1490 have a laser source 1431, a beam expansion lens 1432 expanding a laser beam emitted from the laser source 1431, a collimate lens 1433 converting the laser beam expanded by the beam expansion lens 1432 to parallel rays, and a convergence lens 1434 converging the parallel laser beams whose diameter is enlarged onto the surface of the sample 10. The lateral scattering light detection optics 1440 include, as shown in FIG. 14B, a condenser lens 1441 for condensing lateral scattering light from the sample 10 irradiated with a laser beam and a detector 1442 for detecting the scattering light condensed by the condenser lens 1441.

The stage system 1450 includes a rotatable spindle shaft 1451 on which the sample 10 is placed, a stage 1452 for moving the spindle shaft 1451 in one direction in a plane, and a stage driving unit 1453 for driving the spindle shaft 1451 and the stage 1452.

The general control system 1470 has a signal process/control system 1460, a memory 1471 that stores inspection data and data of inspection parameters, and an input/output unit 1472 having a display screen 1473.

As shown in FIG. 14A, the signal process/control system 1460 includes: an illumination light source control unit 1461 for controlling the laser source 1411 of the high-angle illumination optics 1410 and the laser source 1431 of the low-angle illumination optics 1430; a detection signal processing unit 1462 for receiving output signals of the array sensor 1422 of the regular-reflection light detection optics 1420 and the detector 1442 of the scattering light detection optics 1440, amplifying them, A/D converting the signals to digital signals, and performing signal process on the digital signals to detect a defect candidate; a defect continuity determining unit 1463 for extracting a continuous defect in the sample 10 by using the information of the defect candidate detected by the detection signal processing unit 1462, the information of rotation of the spindle shaft 1451, and the information of the position of the stage 1452; a defect feature amount extracting unit 1464 for extracting a feature amount of the defect detected by the detection signal processing unit 1462 including the continuous defect extracted by the defect continuity determining unit 1463; a defect classifying unit 1465 for classifying a defect by using the information of the feature amount of the defect extracted by the defect feature amount extracting unit 1464; a stage control unit 1466 for controlling the operation of the spindle shaft 1451 and the stage 1452 by controlling the stage driving unit 1453; and an MUP 1467 for controlling the illumination light source control unit 1461, the detection signal processing unit 1462, the defect continuity determining unit 1463, the defect feature amount extracting unit 1464, the defect classifying unit 1465, and the stage control unit 1466.

In a manner similar to the fourth embodiment, the regular-reflection light detection optics 1420 of the regular-reflection light detection optics 1480 directly detect scattering light including regular-reflection light from the sample 10 by the one-dimensional array sensor 1422 without condensing the scattering light by using lenses.

By using the optical magnetic disk inspection apparatus 1400 having such a configuration, defects in the sample 10 can be detected and classified by a method similar to the method described in the fourth embodiment.

Although the present invention achieved by the inventors herein has been concretely described above on the basis of the embodiments, obviously, the present invention is not limited to the foregoing embodiments but can be variously modified without departing from the gist.

The invention may be embodied in other specific forms without departing from the spirit or essential characteristics thereof. The present embodiments are therefore to be considered in all respects as illustrative and not restrictive, the scope of the invention being indicated by the appended claims, rather than by the foregoing description, and all changes which come within the meaning and range of equivalency of the claims are therefore intended to be embraced therein.

The invention claimed is:

1. An optical inspection apparatus comprising:
   a stage which rotates a sample and continuously moves the sample in one direction;
   a light irradiator which irradiates a surface of the sample which is rotated and continuously moved in one direction by the stage, with illumination light which is incident in a direction obliquely to the surface of the sample;
   a first detector which detects an image of light formed by a forward scattering light around an optical axis of regular-reflection light while excluding the regular-reflection light which is reflected from the surface of the sample irradiated with the illumination light from the light irradiator;
   a second detector which condenses and detects lateral scattering light which scatters laterally from the surface of the sample with respect to an incidence direction of the illumination light from the light irradiator; and
   a defect extractor which processes signals detected by the first and the second detector to extract one or more scratch defects in an arbitrary direction in the surface of the sample,
   wherein a shallow defect is extracted from the scratch defects when one of the scratch defect is determined to have a size less than 100 μm and is only detected by the first detector.

2. The optical inspection apparatus according to claim 1, further comprising a third detector which detects regular-reflection light from the surface of the sample excluded by the first detector,
   wherein the defect extractor processes signals detected by the first, second, and third detector to extract a defect including a scratch defect in the surface of the sample.

3. The optical inspection apparatus according to claim 1, wherein the first detector is an array sensor formed by disposing a plurality of detection elements in an array.

4. The optical inspection apparatus according to claim 1, wherein the second detector is an array sensor formed by disposing a plurality of detection elements in an array.

5. An optical inspection apparatus comprising:
   a stage which rotates a sample and continuously moves the sample in one direction;
   a light irradiator which irradiates a surface of the sample which is rotated and continuously moved in one direction by the stage, with illumination light which is incident in a direction obliquely to the surface of the sample;
   a first detector which detects regular-reflection light from the surface of the sample irradiated with the illumination light from the light irradiator;
   a second detector which condenses and detects lateral scattering light which scatters laterally from the surface of the sample with respect to an incidence direction of the illumination light from the light irradiator; and
   a defect extractor which processes signals detected by the first and second detector to extract one or more scratch defects in an arbitrary direction in the surface of the sample,
   wherein a shallow defect is extracted from the scratch defects when one of the scratch defects is determined to have a size less than 100 μm and is only detected by the first detector.

6. The optical inspection apparatus according to claim 5, wherein the first detector is an array sensor formed by disposing a plurality of detection elements in an array.

7. The optical inspection apparatus according to claim 5, wherein the second detector is an array sensor formed by disposing a plurality of detection elements in an array.

8. An optical inspection method comprising the steps of:
   irradiating a surface of a sample which is rotating and continuously moving in one direction with illumination light which is incident in a direction obliquely to the surface of the sample;
   detecting an image of light formed by a forward scattering light around an optical axis of regular-reflection light while excluding the regular-reflection light which is reflected from the surface of the sample irradiated with the illumination light;
   condensing and detecting lateral scattering light which scatters laterally from the surface of the sample with respect to an incidence direction of the illumination light;
   processing a signal obtained by detecting the forward scattering light around the optical axis of the regular-reflection light and a signal obtained by condensing and detecting the lateral scattering light to extract one or more scratch defects in an arbitrary direction in the surface of the sample; and extracting a shallow defect from the scratch defects when one of the scratch defects is determined to have a size less than 100 um and is only detected from the forward scattering light around the optical axis of the regular-reflection light.

9. The optical inspection method according to claim 8, further comprising a step of detecting the regular-reflection light excluded in the step of detecting the image of light, wherein in the step of processing the signal, the signal obtained by detecting the regular-reflection light is processed together with the signal obtained by detecting the forward scattering light and the signal obtained by condensing and detecting the lateral scattering light to extract a defect including a scratch defect in an arbitrary direction in the surface of the sample.

10. The optical inspection method according to claim 8, wherein in the step of detecting the image of light, the forward scattering light around the optical axis of the regular-reflection light is detected by an array sensor formed by disposing a plurality of detection elements in an array.

11. The optical inspection method according to claim 8, wherein in the step of condensing and detecting lateral scattering light, the lateral scattering light is detected by an array sensor formed by disposing a plurality of detection elements in an array.

12. An optical inspection method comprising the steps of:
irradiating a surface of a sample which is rotating and continuously moving in one direction with illumination light which is incident in a direction obliquely to the surface of the sample;

detecting regular-reflection light from the surface of the sample irradiated with the illumination light;

condensing and detecting lateral scattering light which scatters laterally with respect to an incidence direction of the illumination light;

processing a signal obtained by detecting the regular-reflection light and a signal obtained by condensing and detecting the lateral scattering light to extract one or more scratch defects in an arbitrary direction in the surface of the sample; and extracting a shallow defect from the scratch defects when one of the scratch defects is determined to have a size less than 100 μm and is only detected from the regular-reflection light.

13. The optical inspection method according to claim 12, wherein in the step of detecting regular-reflection light, the regular-reflection light is detected by an array sensor formed by disposing a plurality of detection elements in an array.

14. The optical inspection method according to claim 12, wherein in the step of condensing and detecting lateral scattering light, the lateral scattering light is condensed and detected by an array sensor formed by disposing a plurality of detection elements in an array.

* * * * *